(12) United States Patent
Groenendijk et al.

(10) Patent No.: US 9,073,804 B2
(45) Date of Patent: Jul. 7, 2015

(54) ENHANCED CONVERSION OF SYNGAS TO PROPYLENE

(75) Inventors: Peter E. Groenendijk, Hulst (NL); Cornelis Hovingh, Aardenburg (NL)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/883,691

(22) PCT Filed: Dec. 14, 2011

(86) PCT No.: PCT/US2011/064765
§ 371 (c)(1),
(2), (4) Date: May 6, 2013

(87) PCT Pub. No.: WO2012/087687
PCT Pub. Date: Jun. 28, 2012

(65) Prior Publication Data
US 2013/0274356 A1    Oct. 17, 2013

Related U.S. Application Data

(60) Provisional application No. 61/425,359, filed on Dec. 21, 2010.

(51) Int. Cl.
*C07C 1/04* (2006.01)
*C07C 29/16* (2006.01)
*C07C 1/24* (2006.01)

(52) U.S. Cl.
CPC .............. *C07C 1/0485* (2013.01); *C07C 29/16* (2013.01); *C07C 1/04* (2013.01); *C07C 1/24* (2013.01); *C07C 2521/04* (2013.01); *C07C 2521/06* (2013.01)

(58) Field of Classification Search
CPC ............ C07C 1/04; C07C 11/06; C07C 1/24; C07C 29/16; C07C 11/04; C07C 1/0485; C07C 2521/04; C07C 2521/06; C07C 31/10; C07C 1/00
USPC ........................................................ 518/728
See application file for complete search history.

(56) References Cited

U.S. PATENT DOCUMENTS

| | | | |
|---|---|---|---|
| 4,210,426 A | 7/1980 | Sridhar | |
| 4,590,314 A | 5/1986 | Kinkade | |
| 5,227,563 A * | 7/1993 | Fukuhara et al. ............ | 585/640 |
| 6,660,889 B2 | 12/2003 | Fujimoto et al. | |
| 6,713,657 B2 | 3/2004 | O'Rear et al. | |
| 6,768,037 B2 | 7/2004 | O'Rear et al. | |
| 6,982,355 B2 | 1/2006 | Abazajian | |
| 7,517,916 B2 | 4/2009 | Dierickx | |
| 7,642,294 B2 | 1/2010 | Cruijsberg et al. | |
| 2004/0152933 A1 | 8/2004 | O'Rear et al. | |
| 2005/0282916 A1 | 12/2005 | Betts et al. | |
| 2009/0130037 A1 | 5/2009 | Thevenet et al. | |

FOREIGN PATENT DOCUMENTS

| | | |
|---|---|---|
| CN | 1699520 A | 11/2005 |
| CN | 101265149 A | 9/2008 |
| EP | 0149256 A2 | 7/1985 |
| EP | 225143 A2 | 6/1987 |
| WO | 9701521 A1 | 1/1997 |
| WO | 2005037750 A1 | 4/2005 |
| WO | 2005049537 A1 | 6/2005 |
| WO | 2006037806 A1 | 4/2006 |
| WO | WO2008115242 * | 9/2008 |
| WO | 2009054616 A2 | 4/2009 |
| WO | WO2009054616 * | 4/2009 |

OTHER PUBLICATIONS

Unruh "n-Propyl Alcohol", Kirk-Othmer Encyclopedia of Chemical Terminology, Electronic Release, Wiley-VCH, Weinheim 2000, p. 1-8.*
Hedrick, S.A., et al., Activity and selectivity of Group VIII, alkali-promoted Mn-Ni, and Mo-based catalysts for C2+ oxygenate synthesis from the Co hydrogenation and Co/H2/C2H4 reactions, Catalysis Today, 2000, vol. 55, pp. 247-257,Elsevier Science B.V.
Jenner, G., et al., Journal of Molecular Catalysis, 1994, pp. 31-43, vol. 91.
Jordan, Deborah et al., The influence of propylene on carbon monoxide hydrogenation over silica-supported ruthenium, Journal of Catalysis, 1987, pp. 338-350, vol. 107.
Loegdberg, Sara, et al., Applied Catalysis, B: Environmental, 2009, pp. 167-182, vol. 89, Elsevier B.V.
Malyala, Rajeshekaharam V, et al., Selective Production of C4 Hydrocarbons from Syngas in a Dual Reactor Using Co-Ni/ZrO2 and SO42-/ZrO2 Catalysts, 1999, pp. 1323-1334, vol. 38, American Chemical Society.
PCT/US2011/064765, International Search Report and Written Opinion of the International Searching Authority, Apr. 13, 2012.
PCT/US2011/064765, Response to Written Opinion, May 10, 2013.
Reinier J. J. Nel and Arno De Klerk, Fischer-Tropsch Aqueous Phase Refining by Catalytic Alcohol Dehydration, Fischer-Tropsch Refinery Catalysis, Sasol Technology Research and Development, 2007, vol. 46, pp. 3558-3565, American Chemical Society.
Steynberg, et al., Large scale production of high value hydrocarbons using Fischer-Tropsch Technology, 2004, Elsevier B.V.
Subhash CH. Roy, et al., Conversion of syn-gas to lower alkenes over Fe-TiO2-ZnO-K2O catalyst system, Applied Catalysis A, 2001, pp. 153-164.
Yates, et al., The effect of 1-alkene addition on hydrocarbon product distribution in Fischer-Tropsch synthesis on a cobalt catalyst, Dep. Chem. Eng., 1991, Massachusetts Inst. Technol., Cambridge, MA, USA.

* cited by examiner

*Primary Examiner* — Jafar Parsa
*Assistant Examiner* — Amy C Bonaparte

(57) ABSTRACT

Conversion of synthesis gas to propylene is enhanced via a stepped process wherein a Fischer-Tropsch reaction is first carried out, followed by recovery of propylene produced thereby and then use of product ethylene and unreacted syngas in a hydroformylation reaction to produce propanol, which is then dehydrated to form additional propylene. The process enables significant enhancement of propylene yield that is efficient and makes use of ethylene that is a byproduct of Fischer-Tropsch processes that are employed primarily for production of higher olefins, such as hexene and octene. Thus, it can be carried out in conjunction with already on-line Fischer-Tropsch facilities.

7 Claims, No Drawings

ENHANCED CONVERSION OF SYNGAS TO PROPYLENE

This application is a non-provisional application claiming priority from the U.S. Provisional Patent Application No. 61/425,359, filed on Dec. 21, 2010, entitled "ENHANCED CONVERSION OF SYNGAS TO PROPYLENE" the teachings of which are incorporated by reference herein, as if reproduced in full hereinbelow.

BACKGROUND

1. Field of the Invention

This invention relates to the field of converting synthesis gas to propylene. More particularly, it relates to a stepped process wherein unconverted synthesis gas and ethylene, produced via a Fischer-Tropsch reaction, are hydroformylated and then dehydrated to produce additional propylene.

2. Background of the Art

Much research has been devoted to processes using synthesis gas ("syngas"), a mixture of hydrogen gas and carbon monoxide gas, as a starting material. Such processes have been customized to produce a wide variety of desirable olefins, and particularly higher olefins, which are defined herein as those having three or more carbons (C3+). Many of these processes employ a Fischer-Tropsch (FT) reaction, which uses syngas obtained from coal, natural gas, or biomass as a substitute for petroleum starting materials, and employing a metal-based catalyst, such as one based on cobalt (Co), iron (Fe), or ruthenium (Ru). Where these processes are employed to produce olefins, they may be referred to as "Fischer-Tropsch-to-Olefins" (FTO) processes. Unfortunately, such processes tend to produce only small amounts of olefins, and in particular, small amounts of propylene, despite the fact that the propylene may be the dominant product. This may be undesirable where propylene is the production target, particularly for uses as a starting material to make, e.g., polypropylene, acetone, phenol, isopropanol, acrylonitrile, propylene oxide, and/or epichlorohydrin.

Means of enhancing production of propylene have included catalyst substitutions and modifications; modifications of pressure, temperature and feed gas; and alterations of stoichiometries. For example, U.S. Pat. No. 4,590,314 (Kinkade) discloses a selective reaction of a $C_n$ olefin with carbon monoxide (CO) and hydrogen ($H_2$) in the presence of a catalyst consisting essentially of molybdenum sulfide and an alkali metal or alkaline earth metal compound to form a $C_{n+1}$ alcohol. In the formula "n" is a positive integer equal to or greater than 2.

Despite the many substitutions, modifications, and alterations applied to the FTO process over the years, however, there remains in the art a need for processes that can produce propylene, in particular, in larger total amounts.

SUMMARY OF THE INVENTION

In one embodiment the present invention provides a process to prepare propylene comprising the steps of: (a) subjecting a mixture of hydrogen gas and carbon monoxide gas, in the presence of a suitable catalyst, to a Fischer-Tropsch reaction such that a product including propylene, ethylene, unconverted hydrogen gas, and unconverted carbon monoxide gas is formed; (b) recovering at least a portion of the propylene therefrom; (c) subjecting at least a portion of the ethylene, unconverted hydrogen gas and unconverted carbon monoxide gas, in the presence of a suitable catalyst, to a hydroformylation reaction under conditions such that a product including propanol is formed; (d) recovering at least a portion of the propanol; (e) dehydrating at least a portion of the propanol under conditions such that a product including propylene is formed; and (f) recovering at least a portion of the propylene therefrom.

The inventive process offers production of increased amounts of propylene from a single feed of mixed gases, while at the same time being suited for convenient adaptation to any FT production process already in operation because it conveniently employs the ethylene by-product, and also unconverted $H_2$ and CO gases, of such FT process as starting materials for the inventive process's hydroformylation step. It also may be further adapted to include an additional intermediate step, wherein any FT product constituents that are C4 or higher can be cracked to form additional ethylene and propylene; that additional propylene can be also recovered; and that additional ethylene can then be included in the feed to the hydroformylation step. Thus, propylene production may be even further augmented.

DETAILED DESCRIPTION OF THE EMBODIMENTS

It has been found that a classical FT reaction may be conveniently and efficaciously combined with a reductive hydroformylation reaction and a dehydration reaction in order to significantly increase propylene production, particularly in a plant already used for conducting the FT process. The first step of the present invention is the FT reaction of a feed gas mixture of hydrogen ($H_2$) gas and carbon monoxide (CO) gas.

The feed gas mixture for the FT reaction used in the inventive process may be obtained via any means or method used to produce it. Typical reactions to obtain the desirable feed gas mixture constituents may include, in non-limiting example, reacting water ($H_2O$) and CO, which produces $H_2$ gas. In another example, $H_2O$ is combined with methane ($CH_4$) to generate both the CO and the $H_2$ gases. Solid feedstocks, such as coal and biomass, may need to be first gasified to obtain gaseous reactants. Natural gas may be used as a source, and may be economically desirable particularly where such is obtained from stranded gas reserves. In general the $H_2$:CO molar ratio may preferably range from 0.5:1 to 3:1; more preferably from 0.75:1 to 2.5:1; still more preferably from 0.75:1 to 1.25:1; and most preferably from 0.85:1 to 1:1.

In order to carry out the first step of the inventive process, the feed gas contacts a catalyst that is defined herein as an FT catalyst. Suitable FT catalysts may include, but are not necessarily limited to, those comprising transition metals such as iron (Fe), ruthenium (Ru), or combinations thereof. While cobalt (Co) or nickel (Ni) containing catalysts may be effective for the FT process in general and may be selected herein, such are less preferred in the present invention process because of their tendency to favor formation of saturated hydrocarbons or methane, respectively, which results in a less desirable FT product for use in later steps of the inventive process.

In general, catalyst selection for the FT process may also be desirably customized according to the source of the feed gas mixture. For example, Fe-based catalysts may be particularly suitable where a low-hydrogen content synthesis gas is selected, while a Co-based catalyst may be more active for gas mixtures obtained from natural gas, which has a relatively high hydrogen-to-carbon ratio. This is because Fe-based catalysts may be more effective to promote the water-gas-shift reaction occurring when such gases, for example, those derived from coal or biomass, are selected. Similarly, customization may be desirable where a significant level of sulfur-containing compounds will be encountered, because Co-based catalysts "poison" more quickly in the presence of sulfur than do the Fe-based catalysts.

The FT catalyst may be supported or unsupported. In many preferred embodiments, however, the catalyst is either supported or combined with a binder. Such support or binder may be, for example, a ceramic such as silica ($SiO_2$) or alumina ($Al_2O_3$), or a zeolite. High surface area materials, i.e., those having a Brunauer-Emmett-Teller (BET) surface area of at least 300 square meters per gram ($m^2/g$), may be particularly useful.

It is also desirable that a promoter be included with the catalyst. Promoters influence the overall catalyst activity, typically include an alkali metal, and may be included on or in a binder or support material. Useful alkali metals include sodium (Na), potassium (K), cesium (Cs), lithium (Li), and rubidium (Rb), with Na, K, and Cs being particularly preferred. The source of such alkali metals may be any ionic alkali metal compound, such as an oxide, carbonate, sulfate, or combination thereof. Again, care in the selection of the promoter is desirable, because there are combinations of catalyst and promoter that are desirably avoided because of the likelihood of undesirable interactions between them. For example, K is an excellent promoter for Fe-based catalysts. In some cases compounds containing transition metals, such as copper (Cu), may be used as promoters instead of alkali metal compounds.

The FT portion of the inventive process may be desirably carried out at a temperature ranging from 150 degrees Celsius (° C.) to 400° C. In general a temperature ranging from 330° C. to 400° C. is considered to be a "High-Temperature Fischer-Tropsch (HTFT)" reaction. In contrast, a "Low-Temperature Fischer-Tropsch (LTFT)" reaction may be operated from 150° C. to 300° C. In the present invention, however, the preferred temperature range is from 250° C. to 350° C., thereby overlapping both categories. Pressure desirably ranges from 0.1 to 10.1 megapascals (MPa), with a range from 0.10 MPa to 3.04 MPa being more preferred. However, it should be noted that, while increased temperatures and pressures tend to lead to faster reactions and higher conversion rates, such may also tend to favor production of both methane and higher alkanes, i.e., saturation increases. Where the goal of the inventive process is, in one particular embodiment, to enhance overall propylene production, it may be thus desirable to balance the need for rapid and high yield production with total propylene produced. In contrast, where the goal is to employ the present invention in conjunction with an already on-line FT process in order to also convert the ethylene by-product and unconverted syngas to targeted propylene, such balance may be much less desirable. Additionally, the cost of increased temperature and increased pressure, including the inherent cost of appropriate process equipment, may also be a determinative factor in process parameters. Appropriate catalyst selection may be helpful in enabling optimal process parameters for a given production facility.

In the first step of the inventive process, the selected feed gas mixture contacts the catalyst, which may be combined with a selected promoter and/or a selected support and/or binder. This catalyst may be deposed in a suitable reactor, for example, a slurry reactor or a bed-type reactor (e.g., fixed bed, moving bed, or fluidized bed), according to the selected reactor configuration. The gas may be flowed under a variety of operating pressure levels to enable an economically viable production process. The selected flow rate may be influenced by the catalyst selection and process conditions.

The product effluent from the FT portion of the inventive process may contain a variety of paraffins and olefins. Such may include methane, short- and long-chain alkanes, and short-chain olefins. Among these are desirably both ethylene ($C_2H_4$) and propylene ($C_3H_6$). The amounts of these may range, for example, where a Fe-based catalyst is used, from 1 to 6 volume percent (vol %) for ethylene, and from 4 to 15 vol % for propylene, based on all carbon-based products excluding $CO_2$. The traditional product mix for FT reactions is described as an Anderson-Schulz-Flory (ASF) distribution, i.e., it may be described by the ASF equation:

$$W_n/n=(1-\alpha)^2\alpha^{n-1}$$

wherein $W_n$ is the weight fraction of hydrocarbon molecules containing n carbon atoms and $\alpha$ is the chain growth probability, i.e., the probability that a molecule will continue reacting to form a longer chain. Based on this equation, where $\alpha$ is greater, e.g., close to one, the amount of methane formed can be significantly reduced relative to the amounts of longer-chain products. Thus, appropriate selections of catalyst and process parameters may be employed to increase $\alpha$. Such customization may also be useful to alter the FT reaction product distribution to have a higher olefin to paraffin molar ratio, ranging from 2.3:1 to 10:1. In general, relatively low temperature (from 150° C. to 300° C.), relatively low pressure (from 0.10 MPa to 3.04 MPa) and relatively low $H_2$:CO molar ratio (from 0.75:1 to 1.25:1) will tend to increase the olefin to paraffin ratio. In the present invention the propylene is recovered, and any unconverted $H_2$ and CO gases, frequently present in the product in amounts typically ranging, in industrial applications, from 20 vol % to 60 vol %, along with the ethylene, are separated from the FT reaction product to be used in the next step of the invention, which is the hydroformylation reaction.

The hydroformylation reaction step, also known as an oxo synthesis step, is a reductive reaction following the FT step. In this portion of the inventive process an alcohol product (propanol) is formed from the ethylene, (unconverted) CO and (unconverted) $H_2$ gas produced as a result of the FT reaction. The hydroformylation is preferably carried out in the presence of a catalyst. Such alcohol may be formed either directly, or via an intermediate aldehyde (in this case, propanaldehyde), which is then, and, desirably, almost immediately, hydrogenated to form the propanol. As with the FT portion of the inventive process, additional gases may be present in the initial feed into this (hydroformylation) portion of the inventive process, e.g., carbon dioxide ($CO_2$) and/or methanol ($C_3OH$), either of which may serve as a source of CO in the hydroformylation reaction. Furthermore, it may be useful in some embodiments to upgrade the FT product for use in the hydroformylation step, by cracking product components containing four or more carbon atoms, i.e., C4+ compounds, to form more ethylene and propylene at this point, then recovering the propylene and cycling the additional ethylene into the hydroformylation step along with the ethylene that is directly produced by the FT reaction step. Sulfiding agents, such as, for example, hydrogen sulfide ($H_2S$); an alkyl mercaptan; or a dialkyl sulfide or disulfide; may also be present in the FT product, as well as additional hydrocarbons or gas diluents.

The catalyst for the hydroformylation may, in certain embodiments, be any known or conventionally used hydroformylation catalyst. In general suitable catalysts are any that facilitate hydrogenation, and thus may be selected from catalysts including transition metals, such as, for example, Group VIII metals and Group VI metals. Such Group VIII metals may include Fe, Co, Ni, Ru, rhodium (Rh), palladium (Pd), osmium (Os), iridium (Ir), platinum (Pt), and combinations thereof. As is the case with the FT reaction step, however, Fe, Co, Rh, Ni, and combinations thereof are generally preferred, and Co and Rh are particularly preferred. If a Group VI metal is selected, such may be any one or more of chromium (Cr), molybdenum (Mo) and tungsten (W), with Mo being particularly preferred. In general catalysts based on cobalt (Co) and rhodium (Rh) are preferred, with Rh-based catalysts being particularly preferred. However, despite containing Co, the original hydroformylation catalyst, cobalt carbonate (HCo(CO)$_4$), is less preferred.

The selected catalyst may further include either an anion, where such catalyst is a salt, or a ligand, where the catalyst is a coordination complex. Examples of suitable anions may include carbonate ($CO_3^{2-}$ or $CO^{1-}$), an exemplary catalyst being cobalt carbonate (HCo(CO)$_4$), while acetyl acetonate ($C_5H_7O_2^-$, acac) may function as an anion in a salt or may form a coordination complex with some transition metals. Examples of suitable ligands, which may be either ionically or covalently bonded to the metal in a coordination complex, may include, for example, tributylphosphine (PBu$_3$) and related water-soluble ligands, such as triphenylphosphine (TPP, also referred to as PAr$_3$) and its sulfonated analogues. Of these the coordination complexes are preferred catalysts, and in particular embodiments TPP is particularly preferred.

The hydroformylation catalyst may, if desired, be supported or combined with a binder. Suitable materials for use as supports or binders preferably include those selected from silica, titania, zirconia, zinc oxide, magnesium oxide, lanthanum oxide, manganese oxide, and activated carbon. Various clays, including but not limited to hydrotalcite and its many analogues, may also be used.

A catalyst promoter may also be included with the catalyst in the hydroformylation step. Such is desirably selected from the same alkali metals and ionic alkali metal compounds listed hereinabove with respect to the FT portion of the process. However, promoters are not always required and commercially useful hydroformylations, for example, those using rhodium, may be carried out without a promoter per se. Again, as described hereinabove with respect to the FT portion, such are desirably selected to ensure that they act as promoters, and not as poisons, in conjunction with a selected catalyst.

Conditions for the hydroformylation step may include an operating (feed) pressure ranging from 10 to 100 atm (1.0 to 10.1 MPa) and a temperature ranging from 40° C. to 400° C. In certain preferred embodiments an operating pressure ranging from 10 to 40 atm (1.0 to 4.1 MPa) and a temperature ranging from 40° C. to 200° C., preferably from 70° C. to 100° C. may be effective, particularly where a Rh-based catalyst is used. In other embodiments a higher temperature, ranging from 200° C. to 400° C., and more preferably from 250° C. to 350° C., may be employed, particularly where the selected hydroformylation catalyst is Co-based. For convenience it may be desirable to carry out the invention, including the separation(s) that is/are necessary between the FT step and the hydroformylation step, at the same operating pressure.

The feed mixture to the hydroformylation step preferably has a relatively low molar ratio of CO:C$_2$H$_4$, ranging from 0.5:1 to 3:1, more preferably from 0.75:1 to 1.25:1, and most preferably about 1:1, and the H$_2$:CO molar ratio ranges from 1:1 to 3:1, preferably from 1.5:1 to 2.5:1, and most preferably about 2:1.

The result of the hydroformylation reaction is desirably formation of a product that includes predominantly propanol, which is produced via a reaction sequence wherein the ethylene going into the hydroformylation step reacts with the CO to form propanaldehyde, which is then hydrogenated to form propanol. The reaction can be geared toward increased propanol production by means including, for example, allowing additional time of exposure to the hydroformylation catalyst and/or use of a second stage hydrogenation catalyst. If a second stage catalyst is employed, such may, in particular embodiments, be in the form of a slurry of catalyst particles in a non-reactive fluid selected from a group consisting of paraffin solvents, non-paraffin alkane solvents, and oxygenate solvents, including but not limited to products of the FT portion of the inventive process. Alternatively, the second stage catalyst may be situated in an additional fixed, moveable or fluidized bed as part of a sequential processing train.

Where it is decided to employ a second stage hydrogenation catalyst, such may be selected from a group consisting of palladium (Pd), nickel (Ni), copper (Cu), chromium (Cr), iron (Fe), zinc (Zn), silver (Ag), gallium (Ga), tin (Sn), cobalt-molybdenum sulfide (CoMoS$_x$), nickel-molybdenum sulfide (NiMoS$_x$), and iron-molybdenum sulfide (FeMoS$_x$), wherein x represents the number of equivalents of S relative to one equivalent of each of the other elements in each formula. Other suitable second stage hydrogenation catalysts include, for example, those based on copper chromite, copper zinc oxide and/or supported nickel.

Whether two separate hydrogenation catalysts are employed in series, or conditions are suitable to enable suitable hydroformylation in this step with only a single hydrogenation catalyst, the result is desirably a product substantially including propanol, which may then be dehydrated to form propylene. Dehydration may be accomplished by a variety of methods known to those skilled in the art, which may include, for example, entraining the propanol with a carrier gas, such as N$_2$, argon (Ar), or helium (He), that is inert under the reaction conditions, and contacting the gas stream with a suitable dehydration catalyst. Examples of suitable dehydration catalysts may include, in non-limiting embodiments, alumina or gamma-alumina, zinc aluminate, acids such as sulfuric (H$_2$SO$_4$) and phosphoric (H$_3$PO$_4$) acid, and combinations thereof. Desirably the dehydration is carried out at increased temperature, for example, from 200° C. to 500° C., more preferably from 300° C. to 450° C. Because dehydration is an exothermic event, it is desirable that an external cooling means be provided during the reaction for temperature control. Pressure may desirably vary from 0.05 MPa to 3.5 MPa, but a range from 0.1 MPa to 0.7 MPa is more preferred, and equipment may be selected from a variety of reactor types, such as a fixed or fluidized bed, or a slurry reactor. Alternatively, a Chugaev elimination may be carried out, using iodomethane and carbon disulfide to form a xanthate, followed by syn-elimination to form propylene.

The product mixture of either method will usually contain by-products and unreacted starting material, which may be separated from the target propylene product by means which may include, but are not limited to, successive cooling zones, for example, at 50° C., 0° C., and −40° C. In general most of the water and any unreacted propanol will condense at the two higher temperatures, while the target propylene may be recovered at the lowest temperature. Thus, propylene may be recovered both following the FT reaction step and following the hydroformylation reaction step, ultimately representing increased total conversion of the original syngas feed to propylene.

EXAMPLE

An FT catalyst is prepared by mixing 21.33 gram (g) iron (III) oxide (Fe$_2$O$_3$), 2.68 g titanium dioxide (TiO$_2$), 1.25 g graphite (C), 0.50 g potassium carbonate ($K_2CO_3$) and 4.38 g water ($H_2O$) in a crucible. The mixture is dried in air for 12 hours (h) at 120° C. and finally calcined in air for 5 h at 1000° C. The catalyst is crushed to form particles that are U.S. Mesh 20-40 (841-400 microns (μ)). The catalyst is further pre-reduced by exposing it to flowing $H_2$ for 3 h at 425° C. and 0.3 MPa pressure. The catalyst is then incorporated in a fixed bed-type FT reactor.

A gas feed including 22.3 vol % $H_2$, 67.7 vol % CO and 10 vol % He gas (molar ratio $H_2$:CO=0.75) is flowed at a gas hourly space velocity (GHSV) of 1000 milliliters per gram catalyst per hour (mL/g cat/h) through the packed bed for 8 h at 340° C. and 2 MPa operating pressure. Product effluent is analyzed by gas chromatography using multiple columns for separation and both a flame ionization detector (FID) and a thermal conductivity detector (TCD) to analyze for He, $H_2$, CO, $CO_2$, methane ($CH_4$), ethane ($C_2H_6$), ethylene ($C_2H_4$), propylene ($C_3H_6$), propane ($C_3H_8$), and higher boiling components. The internal standard allows for calculating true product yields, and these are reported for the main products in Table 1. Product yield is expressed excluding $CO_2$.

TABLE 1

| Component | Carbon yield (%) |
| --- | --- |
| Methane | 24.2 |
| Ethane | 6.1 |
| Propane | 2.6 |
| Butane | 1.7 |
| Pentane | 1.2 |
| Ethylene | 5.0 |
| Propylene | 12.3 |
| Butene | 5.8 |

* Additional products, including unconverted CO and higher boiling point components, are not listed.

Molar ratios in the product of the FT step of the inventive process, after 8 h on stream, are $H_2$:CO=3.7 and CO:$C_2H_4$=2.6.

The hydroformylation reactor is then charged with acetylacetonate dicarbonyl rhodium, triphenylphosphine (TPP) and propionaldehyde to make a composition of 100 parts per million by weight (wt ppm) Rh and 12 weight percent (wt %) TPP in a total volume of 150 mL. Through this reactor a feed gas including 6.5 mole percent (mol %) ethylene, 19.5 mol % CO and 65 mol % $H_2$ (with the balance being $N_2$) is flowed at various temperatures, pressures and gas hourly space velocities. The product gas flow is analyzed by gas chromatography for ethylene, ethane, propanol and propanal. The conversion (in %), selectivity (in %), and productivity (in moles produced, per liter of reactor volume, per hour, mol/L/h) obtained under the various conditions are shown in Table 2. The main byproduct formed is ethane.

TABLE 2

| Flow (sccm*) | Temperature (° C.) | Pressure (psig**) | $C_2H_6$ conversion (%) | Selectivity to propanol (%) | Productivity (mol/L/h) |
| --- | --- | --- | --- | --- | --- |
| 350 | 85 | 500 | 95 | 99.5 | 0.40 |
| 700 | 85 | 500 | 90.5 | 99.5 | 0.75 |
| 1,000 | 85 | 500 | 86.5 | 99.4 | 1.03 |
| 350 | 100 | 500 | 98.0 | 99.3 | 0.41 |
| 350 | 85 | 300 | 91.7 | 99.4 | 0.38 |

*sccm = standard cubic centimeters per minute.
**pounds per square inch gauge: 500 psig is ~3.45 MPa; 300 psig is ~2.07 MPa.

The propanol is then separated by distillation from the residual syngas and the catalyst. Finally, it is dehydrated by contacting the propanol over a gamma alumina catalyst at 375° C., 8 bar and at a space velocity of 4.7 g/g cat/h to produce propylene at a yield of 99%. The total propylene produced, including both pre- and post-hydroformylation, represents a yield of 19.6%, based on the starting synthesis gas.

What is claimed is:

1. A process to prepare propylene comprising the steps of:
   (a) subjecting a mixture of hydrogen gas and carbon monoxide gas, wherein the hydrogen gas and carbon monoxide gas are present at a $H_2$:CO molar ratio ranging from 0.5:1 to 3:1, in the presence of a suitable catalyst, to a Fischer-Tropsch reaction under conditions such that a product including propylene, ethylene, unconverted hydrogen gas, and unconverted carbon monoxide gas is formed;
   (b) recovering at least a portion of the propylene therefrom;
   (c) subjecting at least a portion of the ethylene, unconverted hydrogen gas and unconverted carbon monoxide gas, wherein the unconverted carbon monoxide gas and ethylene are present at a CO:$C_2H_4$ molar ratio ranging from 0.5:1 to 3:1, and wherein the unconverted hydrogen gas and carbon monoxide gas are present at a $H_2$:CO molar ratio ranging from 1:1 to 3:1, in the presence of a suitable catalyst, to a hydroformylation reaction under conditions such that a product including propanol is formed;
   (d) recovering at least a portion of the propanol therefrom;
   (e) dehydrating at least a portion of the propanol under conditions such that a product including propylene is formed; and
   (f) recovering at least a portion of the propylene therefrom.

2. The process of claim 1 wherein in step (c) the $H_2$:CO molar ratio is 2:1.

3. The process of claim 1 wherein the conditions in step (a) include at least one of a temperature ranging from 150° C. to 400° C.; a pressure ranging from 0.10 MPa to 10.13 MPa; or a combination thereof.

4. The process of claim 1 wherein the conditions in step (c) include a temperature ranging from 40° C. to 400° C.; a pressure ranging from 1.0 MPa to 10.1 MPa; or a combination thereof.

5. The process of claim 1 wherein the conditions in step (c) include at least one of a temperature ranging from 70° C. to 100° C.; a pressure ranging from 1.0 MPa to 4.1 MPa; or a combination thereof.

6. The process of claim 1 wherein the conditions in step (e) include at least one of a temperature ranging from 200° C. to 500° C.; a pressure ranging from 0.05 MPa to 3.5 MPa; or a combination thereof.

7. The process of claim 1 wherein the product of step (a) further includes C4+ compounds, and the C4+ compounds are cracked to form additional ethylene and additional propylene, and at least a portion of the additional ethylene is added to the ethylene used in step (c), and at least a portion of the additional propylene is recovered.

* * * * *